United States Patent
Hershey et al.

(10) Patent No.: US 11,623,097 B2
(45) Date of Patent: *Apr. 11, 2023

(54) PULSE GENERATOR SYSTEM FOR PROMOTING DESYNCHRONIZED FIRING OF RECRUITED NEURAL POPULATIONS

(71) Applicant: Boston Scientific Neuromodulation Corporation, Valencia, CA (US)

(72) Inventors: Bradley L. Hershey, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/199,185

(22) Filed: Mar. 11, 2021

(65) Prior Publication Data
US 2021/0196959 A1    Jul. 1, 2021

Related U.S. Application Data

(63) Continuation of application No. 16/417,076, filed on May 20, 2019, now Pat. No. 10,960,211, which is a
(Continued)

(51) Int. Cl.
*A61N 1/36* (2006.01)
*A61N 1/00* (2006.01)
(Continued)

(52) U.S. Cl.
CPC .......... *A61N 1/36139* (2013.01); *A61N 1/00* (2013.01); *A61N 1/3605* (2013.01);
(Continued)

(58) Field of Classification Search
CPC .. A61N 1/36139; A61N 1/00; A61N 1/36017; A61N 1/36021; A61N 1/3605;
(Continued)

(56) References Cited

U.S. PATENT DOCUMENTS

| 5,697,958 A | 12/1997 | Paul et al. |
| 5,702,429 A | 12/1997 | King |

(Continued)

FOREIGN PATENT DOCUMENTS

| WO | 2006/029090 | 3/2006 |
| WO | 2017/100866 | 6/2017 |

(Continued)

OTHER PUBLICATIONS

H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).

(Continued)

*Primary Examiner* — Paula J Stice
(74) *Attorney, Agent, or Firm* — Lewis & Reese, PLLC

(57) ABSTRACT

An Implantable Pulse Generator (IPG) is disclosed that is capable of sensing a degree to which recruited neurons in a patient's tissue are firing synchronously, and of modifying a stimulation program to promote desynchronicity and to reduce paresthesia. An evoked compound action potential (ECAP) of the recruited neurons is sensed as a measure of synchronicity by at least one non-active electrode. An ECAP algorithm operable in the IPG assesses the shape of the ECAP and determines one or more ECAP shape parameters that indicate whether the recruited neurons are firing synchronously or desynchronously. If the shape parameters indicate significant synchronicity, the ECAP algorithm can adjust the stimulation program to promote desynchronous firing.

20 Claims, 11 Drawing Sheets

Related U.S. Application Data continuation of application No. 15/428,612, filed on Feb. 9, 2017, now Pat. No. 10,406,368.

(60) Provisional application No. 62/324,801, filed on Apr. 19, 2016.

(51) Int. Cl.
*A61B 5/00* (2006.01)
*A61B 5/24* (2021.01)

(52) U.S. Cl.
CPC ..... *A61N 1/36017* (2013.01); *A61N 1/36021* (2013.01); *A61N 1/36071* (2013.01); *A61N 1/36128* (2013.01); *A61B 5/24* (2021.01); *A61B 5/40* (2013.01); *A61N 1/36125* (2013.01)

(58) Field of Classification Search
CPC ............ A61N 1/36071; A61N 1/36128; A61N 1/36125; A61B 5/24; A61B 5/40
See application file for complete search history.

(56) References Cited

U.S. PATENT DOCUMENTS

| | | | |
|---|---|---|---|
| 5,814,092 A | 9/1998 | King | |
| 5,902,236 A | 5/1999 | Iversen | |
| 5,902,249 A | 5/1999 | Lyster | |
| 5,913,882 A | 6/1999 | King | |
| 6,078,838 A | 6/2000 | Rubinstein | |
| 6,181,969 B1 | 1/2001 | Gord et al. | |
| 6,516,227 B1 | 2/2003 | Meadows et al. | |
| 6,907,130 B1 | 6/2005 | Rubinstein et al. | |
| 7,024,247 B2 | 4/2006 | Gliner et al. | |
| 7,424,322 B2 | 9/2008 | Lombardi et al. | |
| 7,450,992 B1 | 11/2008 | Cameron | |
| 8,255,057 B2 | 8/2012 | Fang et al. | |
| 8,335,569 B2 | 12/2012 | Aghassian | |
| 8,335,664 B2 | 12/2012 | Eberle | |
| 8,352,030 B2 | 1/2013 | Denison | |
| 8,412,345 B2 | 4/2013 | Moffitt | |
| 8,463,400 B2 | 6/2013 | Hegi et al. | |
| 8,498,716 B2 | 7/2013 | Chen et al. | |
| 8,606,362 B2 | 12/2013 | He et al. | |
| 8,620,436 B2 | 12/2013 | Parramon et al. | |
| 8,768,453 B2 | 7/2014 | Parramon et al. | |
| 8,913,804 B2 | 12/2014 | Blum et al. | |
| 9,044,155 B2 | 6/2015 | Strahl | |
| 9,061,140 B2 | 6/2015 | Shi et al. | |
| 9,119,964 B2 | 9/2015 | Marnfeldt | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri et al. | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 2002/0156513 A1 | 10/2002 | Borkan | |
| 2005/0246004 A1 | 11/2005 | Cameron et al. | |
| 2008/0146894 A1 | 6/2008 | Bulkes et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2012/0116475 A1 | 5/2012 | Nelson et al. | |
| 2013/0289665 A1 | 10/2013 | Marnfeldt et al. | |
| 2014/0100632 A1 | 4/2014 | Rao et al. | |
| 2014/0194772 A1 | 7/2014 | Single et al. | |
| 2014/0236042 A1 | 8/2014 | Parker et al. | |
| 2014/0257428 A1 | 9/2014 | Zhu | |
| 2014/0277281 A1 | 9/2014 | Grandhe | |
| 2014/0296737 A1 | 10/2014 | Parker et al. | |
| 2015/0012061 A1 | 1/2015 | Chen | |
| 2015/0018898 A1 | 1/2015 | Tass | |
| 2015/0080982 A1 | 3/2015 | Funderburk | |
| 2015/0157861 A1 | 6/2015 | Aghassian et al. | |
| 2015/0246230 A1 | 9/2015 | Litvak | |
| 2015/0282725 A1 | 10/2015 | Single et al. | |
| 2015/0313487 A1 | 11/2015 | Single et al. | |
| 2015/0360038 A1 | 12/2015 | Zottola et al. | |
| 2015/0374999 A1 | 12/2015 | Parker et al. | |
| 2016/0166164 A1 | 6/2016 | Obradovic et al. | |
| 2016/0228705 A1 | 8/2016 | Crowder | |
| 2016/0287126 A1 | 10/2016 | Parker et al. | |
| 2016/0287182 A1 | 10/2016 | Single et al. | |
| 2016/0303368 A1 | 10/2016 | Parramon et al. | |
| 2017/0049345 A1 | 2/2017 | Single et al. | |
| 2017/0071490 A1 | 3/2017 | Parker et al. | |
| 2017/0135624 A1 | 5/2017 | Parker et al. | |
| 2017/0216587 A1 | 8/2017 | Parker et al. | |
| 2017/0281958 A1 | 10/2017 | Serrano Carmona et al. | |
| 2017/0281959 A1 | 10/2017 | Serrano Carmona et al. | |
| 2017/0296823 A1 | 10/2017 | Hershey et al. | |
| 2017/0361101 A1 | 12/2017 | Single et al. | |
| 2018/0071527 A1 | 3/2018 | Feldman et al. | |
| 2018/0110987 A1 | 4/2018 | Parker et al. | |
| 2018/0117335 A1 | 5/2018 | Parker et al. | |
| 2018/0132747 A1 | 5/2018 | Parker et al. | |
| 2018/0132760 A1 | 5/2018 | Parker et al. | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |
| 2019/0275331 A1 | 9/2019 | Zhu | |
| 2019/0290900 A1 | 9/2019 | Esteller et al. | |
| 2019/0299006 A1 | 10/2019 | Marnfeldt | |
| 2019/0366094 A1 | 12/2019 | Esteller et al. | |
| 2020/0155019 A1 | 5/2020 | Esteller et al. | |
| 2020/0305745 A1 | 10/2020 | Wagenbach et al. | |

FOREIGN PATENT DOCUMENTS

| | | |
|---|---|---|
| WO | 2017/173493 | 10/2017 |
| WO | 2017/219096 | 12/2017 |

OTHER PUBLICATIONS

M. Moffit et al., A Novel 3-Dimensional Algorithm for Model-Based Programming in Spinal Cord Stimuation (SCS): Illumina-3D™, presentation (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19th NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

(56) References Cited

OTHER PUBLICATIONS

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).
International Search Report and Written Opinion regarding corresponding PCT Application No. PCT/US2017/017313, dated Apr. 21, 2017.

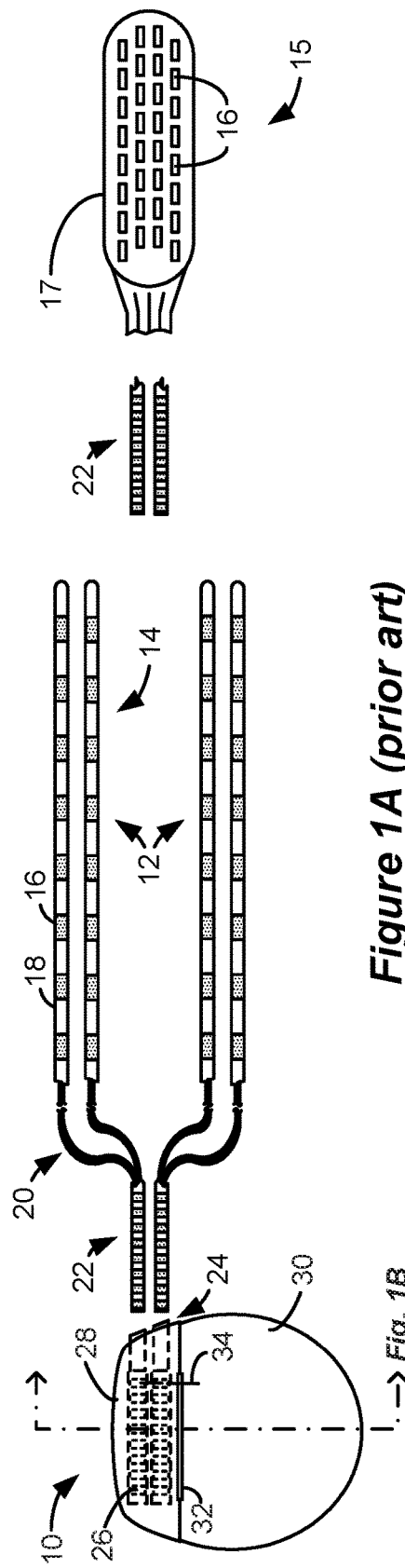
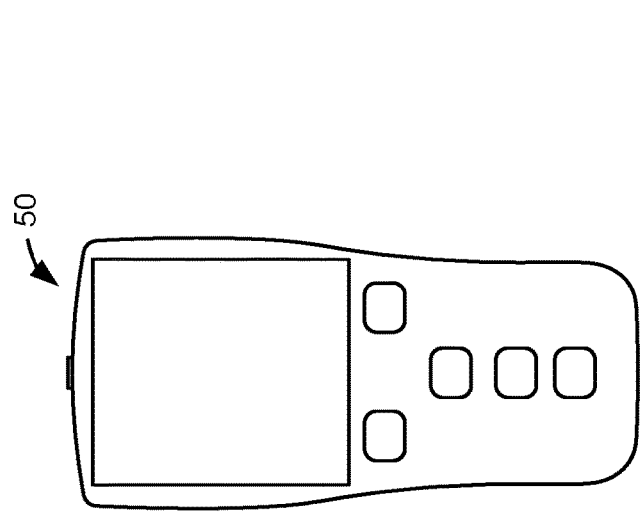
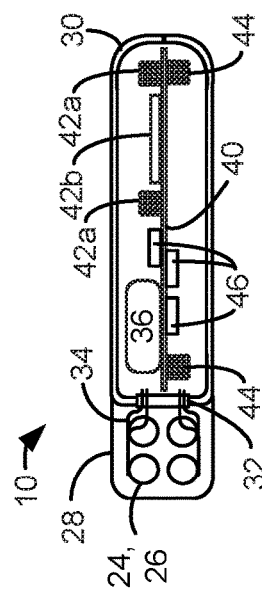
Figure 1A (prior art)
Figure 1B (prior art)
Figure 2 (prior art)

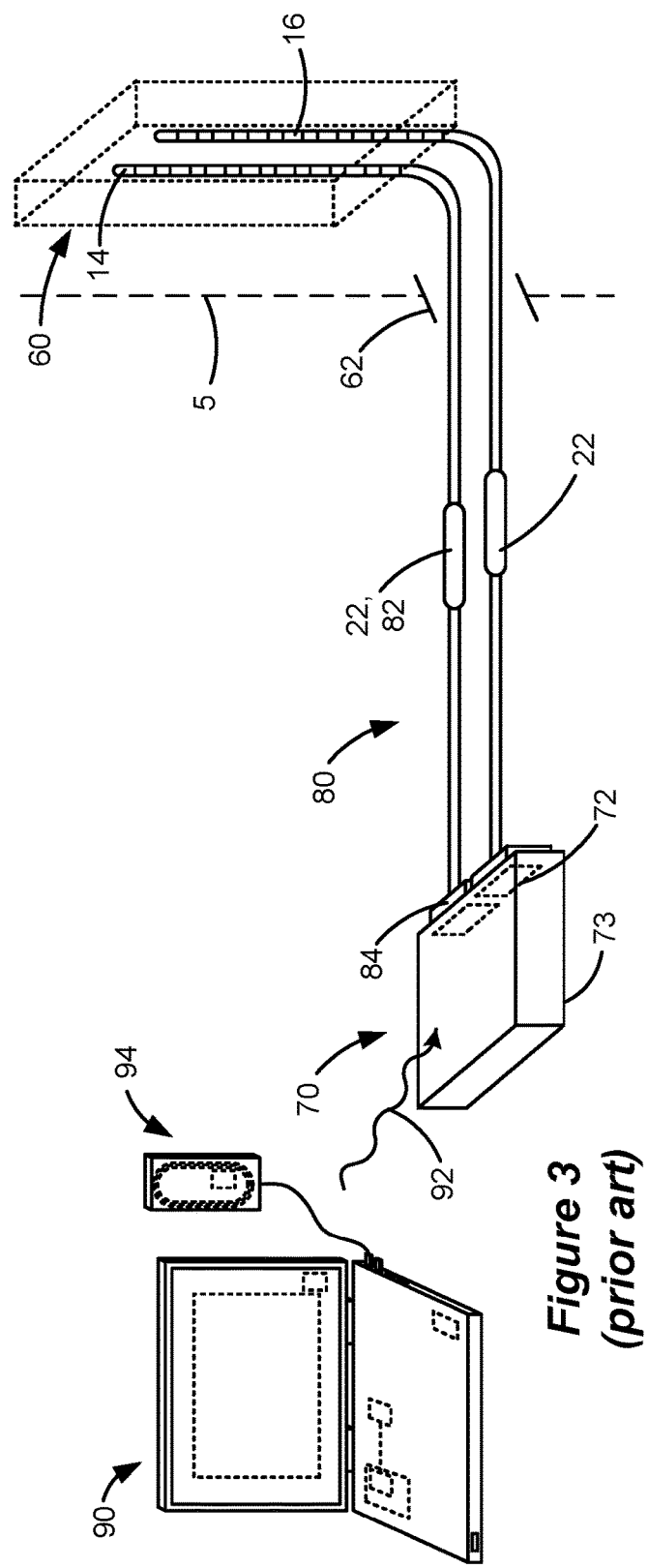
*Figure 3 (prior art)*
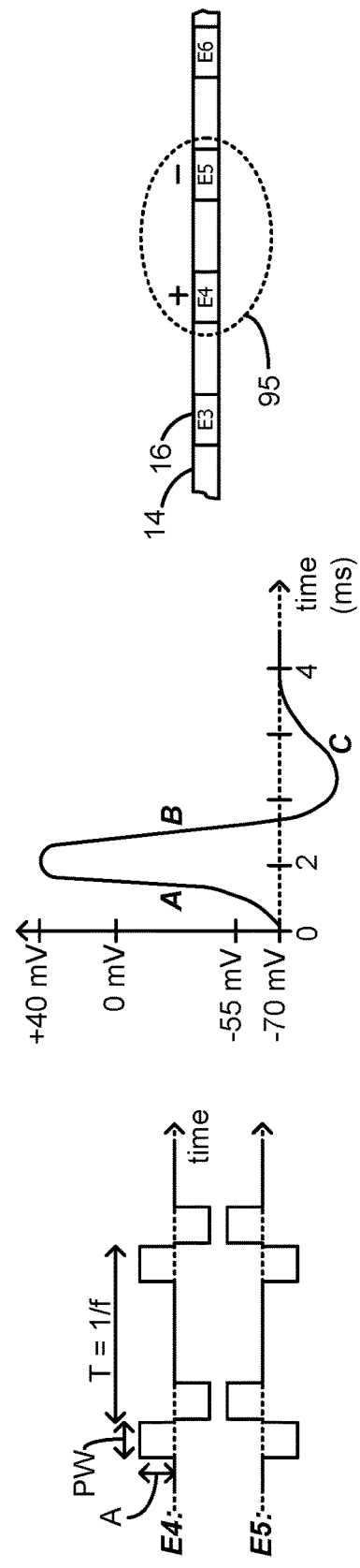
*Figure 6 (prior art)*
*Figure 5 (prior art)*
*Figure 4 (prior art)*

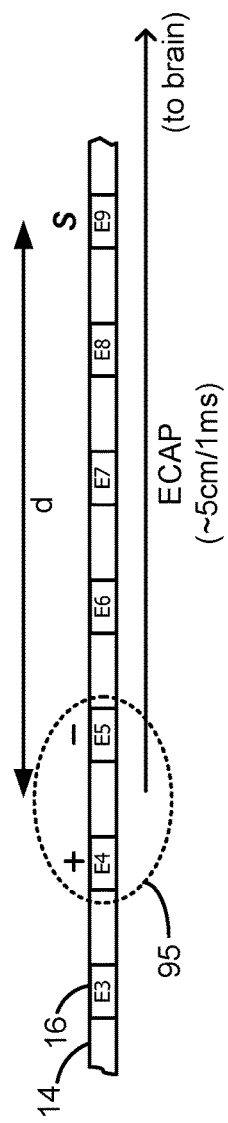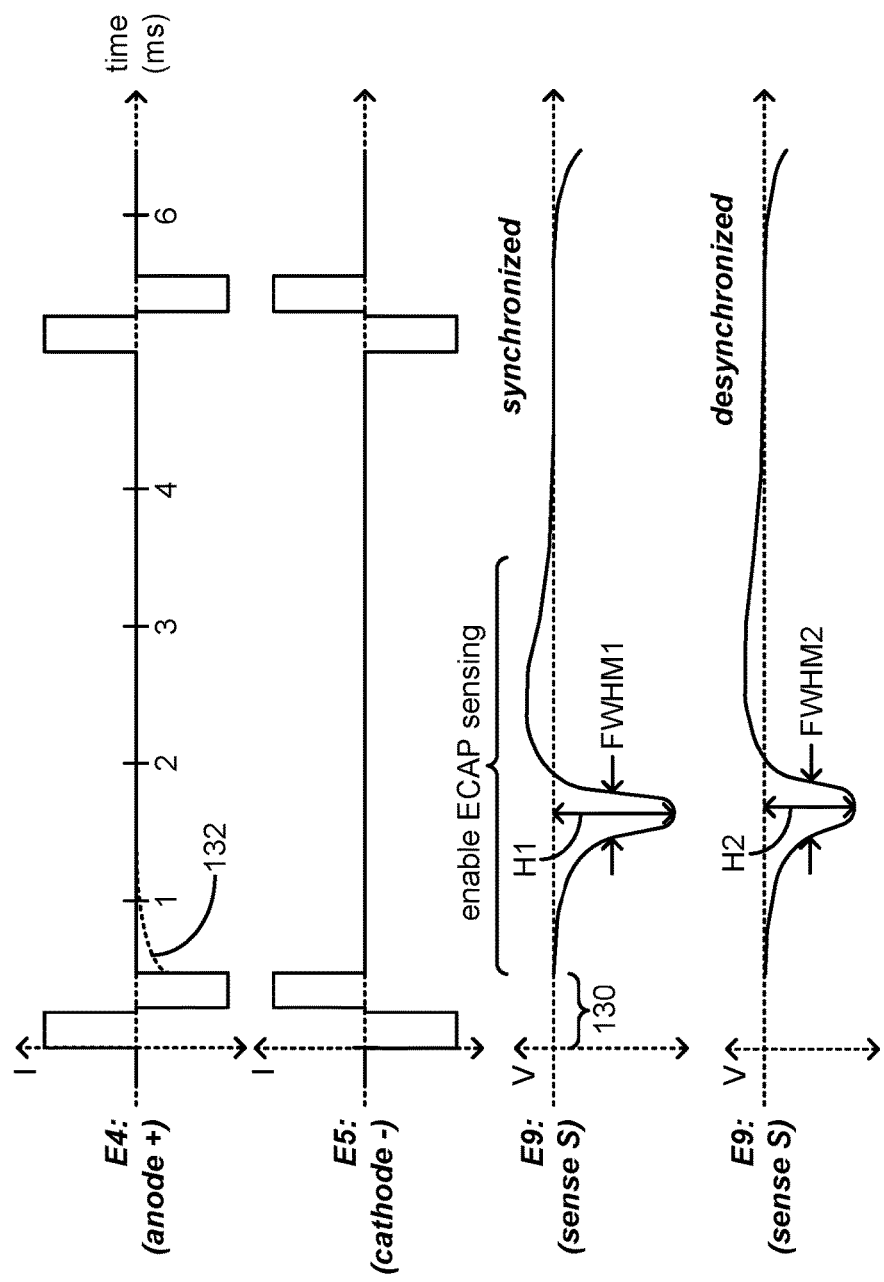
Figure 8A
Figure 8B

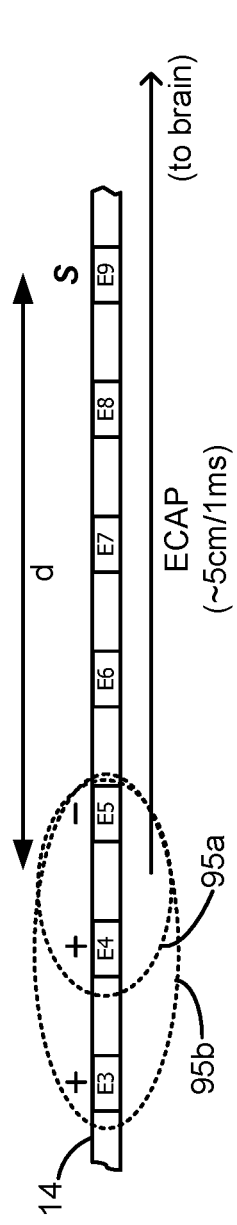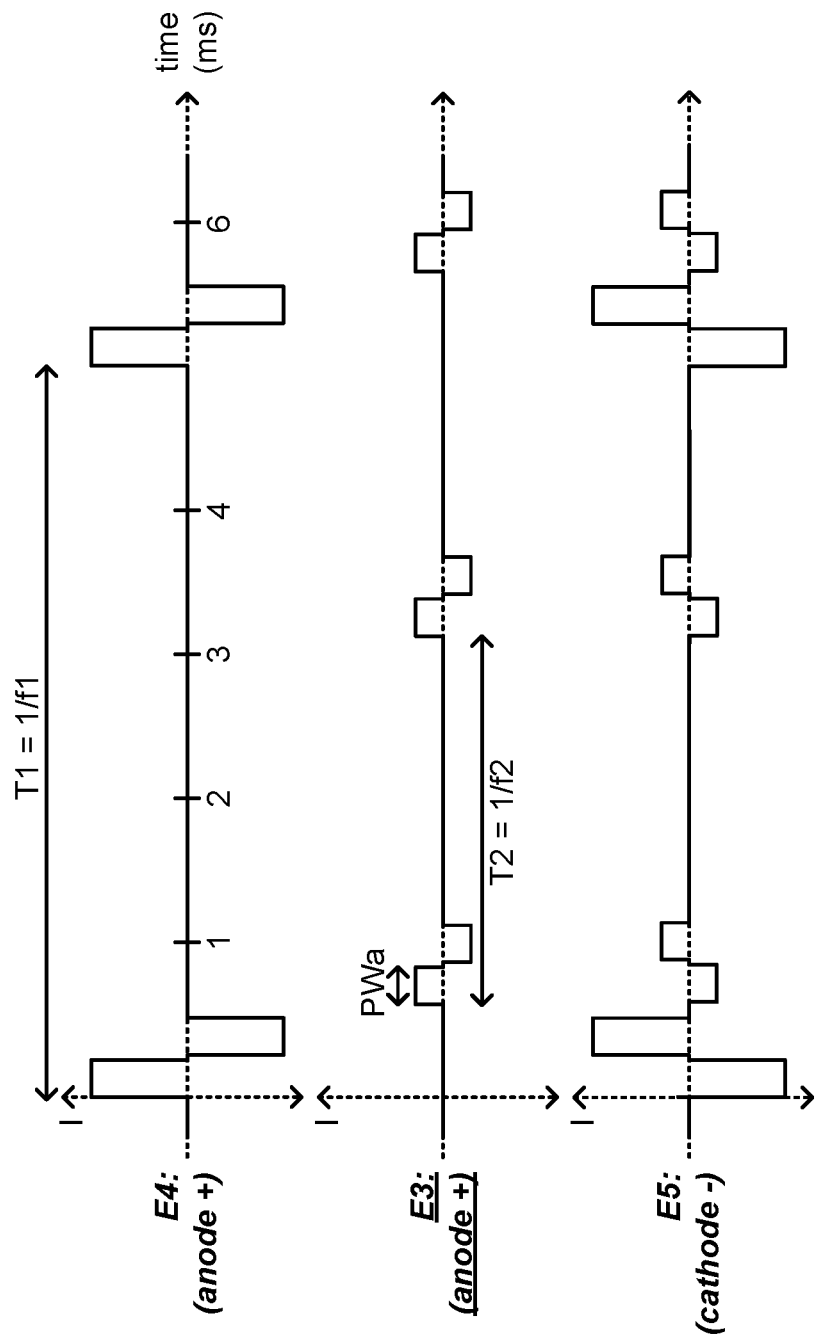
Figure 13A
Figure 13B

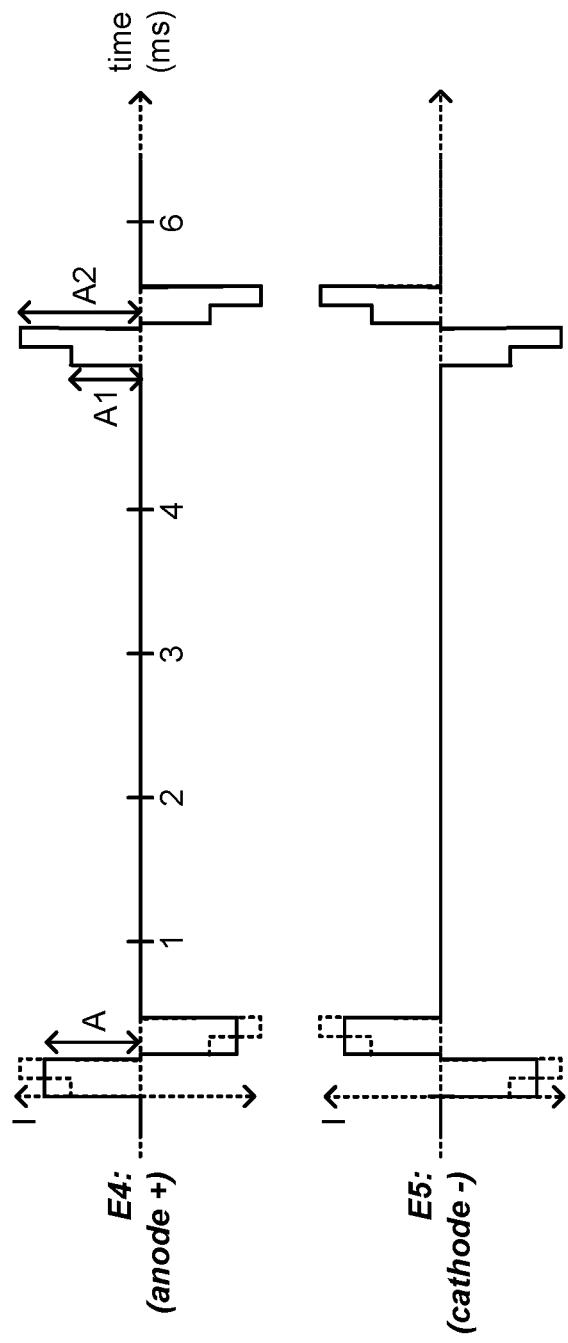

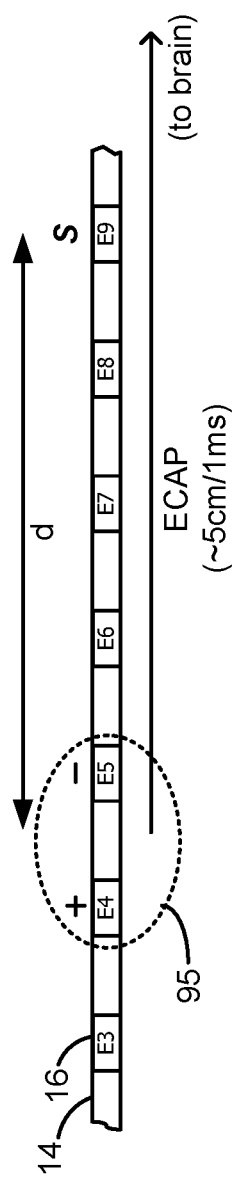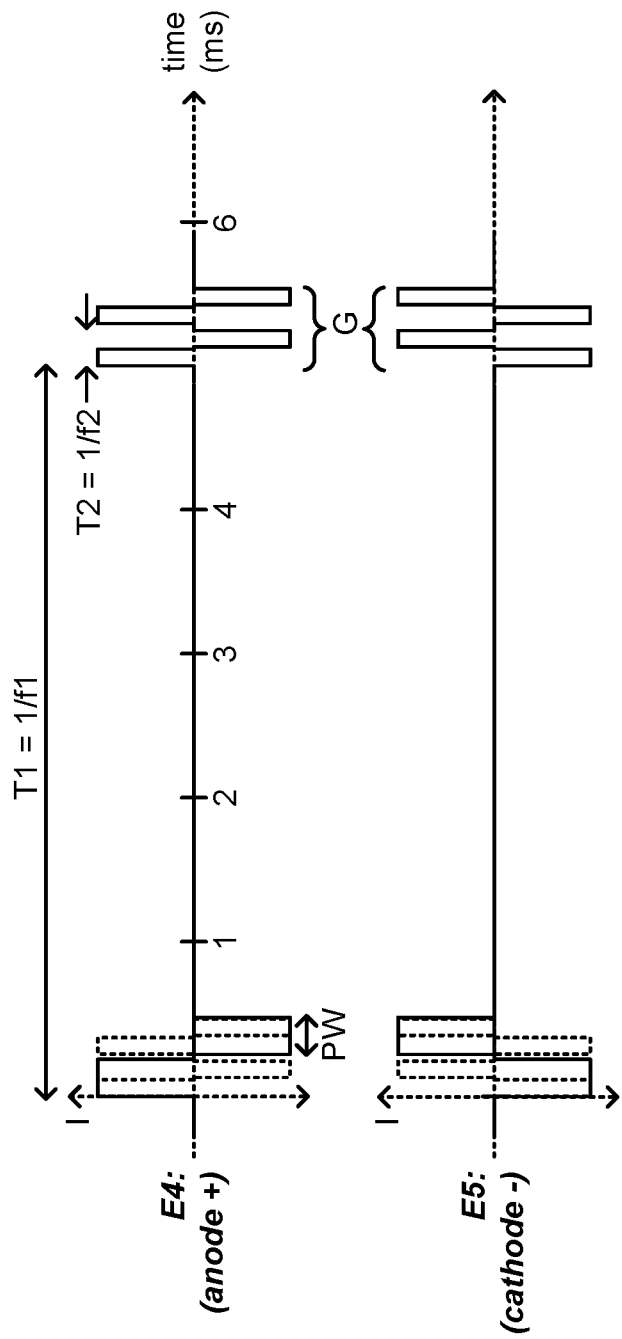

PULSE GENERATOR SYSTEM FOR PROMOTING DESYNCHRONIZED FIRING OF RECRUITED NEURAL POPULATIONS

CROSS REFERENCE TO RELATED APPLICATIONS

This is a continuation application of U.S. patent application Ser. No. 16/417,076, filed May 20, 2019 (now U.S. Pat. No. 10,960,211), which is a continuation application of U.S. patent application Ser. No. 15/428,612, filed Feb. 9, 2017 (now U.S. Pat. No. 10,406,368), which is a non-provisional of U.S. Provisional Patent Application Ser. No. 62/324,801, filed Apr. 19, 2016. These applications are incorporated by reference in their entirety, and priority is claimed to each.

FIELD OF THE INVENTION

The present invention relates generally to medical device systems, and more particularly to a pulse generator system operable to promote desynchronized firing of recruited neural populations.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14, with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; a telemetry antenna—42a and/or 42b—for wirelessly communicating data with an external controller 50 (FIG. 2); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

Either or both of telemetry antennas 42a and 42b can be used to transcutaneously communicate data through the patient's tissue to an external device such as the external controller 50 shown in FIG. 2. Antennas 42a and 42b are different in shape and in the electromagnetic fields they employ. Telemetry antenna 42a comprises a coil, which can bi-directionally communicate with an external device via a magnetic induction communication link, which comprises a magnetic field of typically less than 10 MHz operable in its near-field to communicate at a distance of 12 inches or less for example. Telemetry antenna 42b comprises a short-range Radio-Frequency (RF) antenna that operates in accordance with a short-range RF communication standard and its underlying modulation scheme and protocol to bi-directionally communicate with an external device along a short-range RF communication link. Short-range RF communication link typically operates using far-field electromagnetic waves ranging from 10 MHz to 10 GHz or so, and allows communications between devices at distances of about 50 feet or less. Short-range RF standards operable with antenna 42b include, for example, Bluetooth, BLE, NFC, Zigbee, WiFi (802.11x), and the Medical Implant Communication Service (MICS) or the Medical Device Radiocommunications Service (MDRS). Short-range RF antenna 42b can take any number of well-known forms for an electromagnetic antenna, such as patches, slots, wires, etc., and can operate as a dipole or a monopole. IPG 10 could contain both the coil antenna 42a and the short-range RF antenna 42b to broaden the types of external devices with which the IPG 10 can communicate, although IPG 10 may also include only one of antenna 42a and 42b.

Implantation of IPG 10 in a patient is normally a multi-step process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may specify for example which of the electrodes 16 are to be active and used to issue stimulation pulses; whether those active electrodes are to act as anodes or cathodes; the current or voltage amplitude (A) of the stimulation pulses; the pulse width (PW) of the stimulation pulses; and frequency (f) of the stimulation pulses, as well as other parameters.

The clinician programmer system of FIG. 3 can also be used generally by a clinician to communicate with and program the IPG 10 once it is fully implanted in a patient. Such communication again would occur via communication link 92. Thus the clinician programmer system may be used during patient check-ups for example to update the stimulation program the IPG 10 is running.

An example of stimulation pulses as prescribed by a particular stimulation program is illustrated in FIG. 4. As shown, and as is typical in an IPG, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases.

Biphasic pulses are useful because the second pulse phase can actively recover any charge build up after the first pulse phase residing on capacitances (such as the DC-blocking capacitors 107 discussed later with respect to FIG. 7) in the current paths between the active electrodes. In the example stimulation program shown, electrode E4 is selected as the anode electrode while electrode E5 is selected as the cathode electrode. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively.

Referring again to FIG. 3, the stimulation program executed by the ETS 70 can be provided or adjusted via a wired or wireless link 92 (wireless shown) from a clinician programmer 90. As shown, the clinician programmer 90 comprises a computer-type device, and may communicate wirelessly with the ETS 70 via link 92, which link may comprise magnetic inductive or short-range RF telemetry schemes as already described. Should the clinician programmer 90 lack a communication antenna, a communication head or wand 94 may be wired to the computer which has a communication antenna. Thus, the ETS 70 and the clinician's programmer 90 and/or its communication head 94 may include antennas compliant with the telemetry scheme chosen. Clinician programmer 90 may be as described in U.S. Patent Application Publication 2015/0360038. External controller 50 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure.

By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined during the trial stimulation phase, it/they can then be programmed into the IPG 10, and thereafter modified wirelessly, using either the external programmer 50 or the clinician programmer 90.

BRIEF DESCRIPTION OF THE DRAWINGS

FIGS. 1A and 1B respectively show an Implantable Pulse Generator (IPG) in plan and cross sectional views, in accordance with the prior art.

FIG. 2 shows a hand-held external controller for communicating with an IPG, in accordance with the prior art.

FIG. 3 shows a clinician programming system for communicating with an IPG or an External Trial Stimulator (ETS), in accordance with the prior art.

FIG. 4 shows an original stimulation program deemed effective for a patient, in accordance with the prior art.

FIG. 5 shows a graph of an action potential of a neuron, in accordance with the prior art.

FIG. 6 shows an electric field produced in a patient's tissue for recruiting neurons to fire, in accordance with the prior art.

FIGS. 8A and 8B show an original stimulation program, the resulting generation of an ECAP (with examples of resulting synchronous and desynchronous ECAPs), and detection of that ECAP by ECAP algorithm in the improved IPG, in accordance with an example of the invention.

FIGS. 13A and 13B show a fourth manner in which the additional active electrode produces pulses with a frequency different from the pulses in the original stimulation program, in accordance with an example of the invention.

FIGS. 14A and 14B show a fifth manner not using an additional active electrode, in which the amplitude of the pulses in the original stimulation program is modified, in accordance with an example of the invention.

FIGS. 15A and 15B show a sixth manner not using an additional active electrode, in which the pulse widths of the pulses in the original stimulation program are modified, in accordance with an example of the invention.

DETAILED DESCRIPTION

Figure 7:
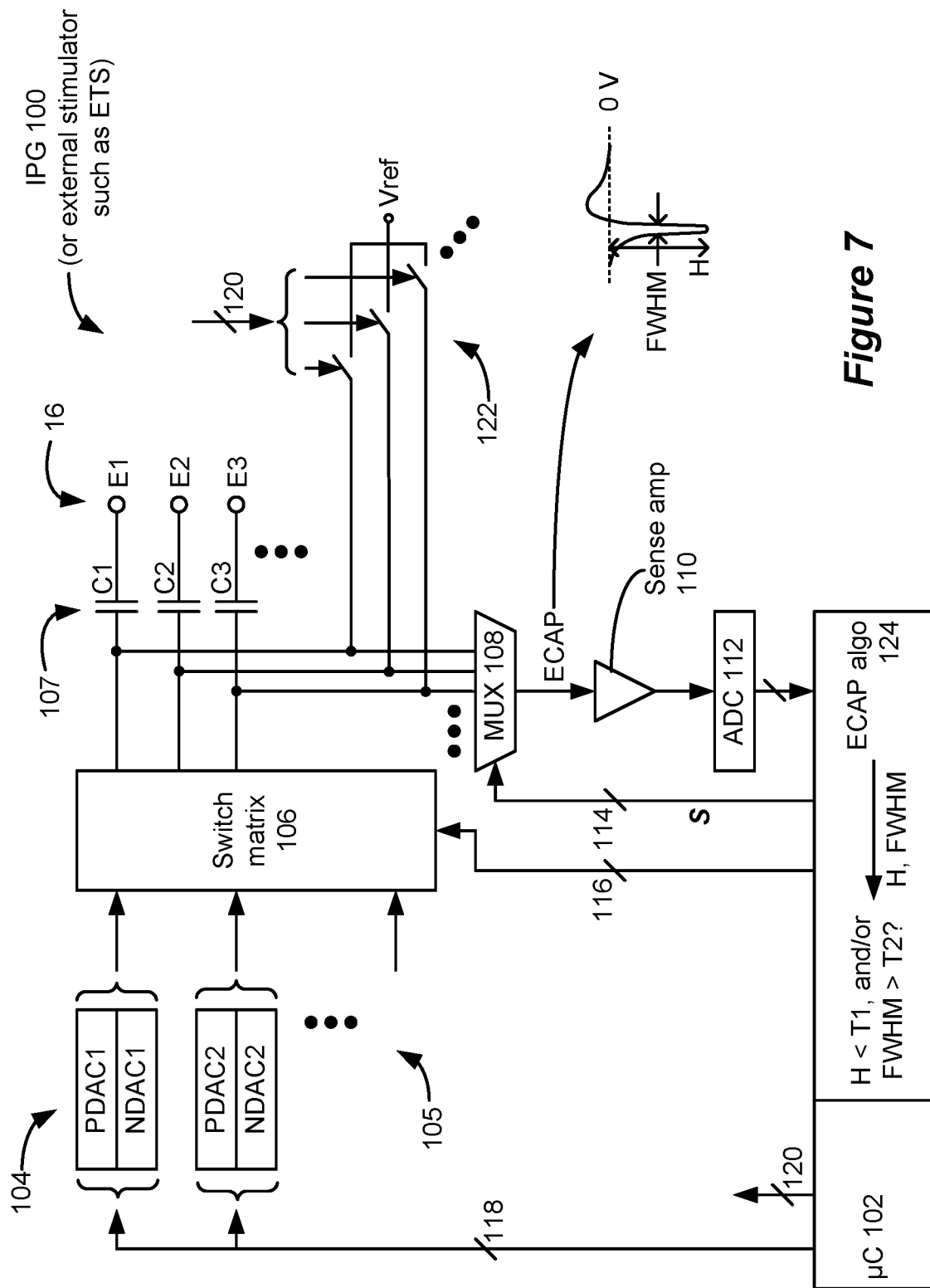
FIG. 7 shows an improved IPG including control circuitry programmed with an Evoked Compound Action Potential (ECAP) algorithm, and further including sensing circuitry for sensing an ECAP at a sense electrode, in accordance with an example of the invention.

Particularly as concerns SCS therapy, there is evidence to suggest that providing stimulation pulses at relatively high frequencies (e.g., >1 kHz) can have therapeutic benefits when compared to lower-frequency stimulation pulses. In particular, it has been reported that higher-frequency stimulation may reduce certain side effects that can accompany lower-frequency stimulation. Specifically, higher-frequency stimulation may reduce paresthesia—a tingling or prickling sensation.

The inventor theorizes that the benefits of high frequency stimulation relate to inherent limitations regarding the frequency at which neurons can respond to stimulation. When a neuron is recruited by electrical stimulation, it will issue an action potential—that is, the neuron will "fire." An action potential for a typical neuron is shown in FIG. 5. Should electrical recruitment cause the neuron's resting state (e.g., –70 mV as measured from inside the cell) to exceed a threshold (e.g., –55 mV), the neuron will depolarize ("A"), repolarize ("B"), and refract ("C") before coming to rest again. If electrical stimulation continues, the neuron will fire again at some later time. Note that the action potential does not change in magnitude for a given neuron; in other words, the action potential does not change with the strength of stimulation. Instead, a strong stimulus will increase the frequency at which action potentials are issued.

However, there is a limit to how quickly a given neuron can fire. Each neuron is unique in its shape and size, and thus can fire at its own inherent maximum frequency. Consider FIG. 6, which illustrates the example of FIG. 4 in which electrodes E4 and E5 on lead 14 are used to produce pulses. Such stimulation produces an electric field in a volume 95 of the patient's tissue 5 around the selected electrodes. Some of the neurons within the electric field volume 95 will be recruited and fire, particularly those proximate to the cathodic electrode E5. Hopefully the sum of the neurons firing within volume 95 will mask signals indicative of pain, thus providing the desired therapy.

The inventor reasons that if high frequency stimulation is used that is generally higher than the maximum frequency at which the neurons can fire (and if the stimulation is suitably strong), the recruited neurons within volume 95 will be unable to fire at the frequency of the stimulation. Instead, each neuron will be limited to firing at its maximum frequency, which again will be different for each neuron. Thus, the firing of the neurons within volume 95 will be desynchronized with different neurons firing at different times. By contrast, the inventor hypothesizes that if low frequency stimulation is used that is generally lower than the maximum neuronal frequency, the recruited neurons within volume 95 will all fire at the frequency of the stimulation and at the same time. In other words, the neurons will fire synchronously.

The inventor reasons further that synchronous firing of the neurons at low frequencies is responsible for the undesired side effect of paresthesia, and that desynchronized firing at higher frequencies mitigates this effect. However, the inventor finds this circumstance unfortunate, because it is not a simple matter to provide stimulation pulses at high frequencies. For one, high frequency stimulation requires that the circuitry that produces the pulses in the IPG 10 also switch at high frequencies. High frequency switching of the IPG's circuitry is more power consumptive, and thus requires a higher draw from the IPG battery 36. As a result, the battery 36 must either be made bigger increasing IPG size, or the battery must be wirelessly recharged more frequently, both of which are undesired.

The inventor thus provides an IPG or ETS that is capable of sensing the degree to which recruited neurons are firing synchronously. Sensed synchronicity is preferably also used in a closed loop fashion by the IPG to modify an original stimulation program the IPG is executing, which original stimulation program is otherwise generally providing good therapeutic result for the patient, although perhaps with the side effect of paresthesia. In one example, a neural response to the original stimulation program, particularly an evoked compound action potential (ECAP) of the recruited neurons, is sensed as a measure of synchronicity. At least one non-active electrode senses the resulting ECAP, which is digitized and sent to the IPG's control circuitry. An ECAP algorithm assesses the shape of the ECAP and determines one or more ECAP shape parameters that indicate whether the recruited neurons are firing synchronously or desynchronously. If the shape parameters indicate a high degree of synchronicity, the ECAP algorithm can adjust the stimulation program in one or more manners to promote desynchronous firing, thus reducing paresthesia. The ECAP algorithm can operate to adjust an original stimulation program even if it is otherwise operable at generally low frequencies (<1 kHz), although it can be used to assess and promote desynchronicity at higher frequencies as well.

An improved IPG 100 operable as just described is shown in FIG. 7. Although described in the context of an IPG 100, it should be realized that the invention could also be embodied in an external stimulator, such as an External Trial Stimulation (e.g., ETS 70, FIG. 3) that generally mimics the operation of an IPG as explained earlier.

The IPG 100 includes control circuitry 102 into which an ECAP algorithm 124 can be programmed, which may comprise a microcontroller for example such as Part Number MSP430, manufactured by Texas Instruments, which is described in data sheets posted on the Internet. Other types of control circuitry may be used in lieu of a microcontroller as well, such as microprocessors, FPGAs, DSPs, or combinations of these, etc. Control circuitry may also be formed in whole or in part in one or more Application Specific Integrated Circuits (ASICs), as described in U.S. Patent Application Publication 2012/0095529 and U.S. Pat. Nos. 9,061,140 and 8,768,453, which are incorporated herein by reference.

A bus 118 provides digital control signals to stimulation circuitry 105, including one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. A switch matrix 106 is used to route one or more PDACs and one or more NDACs to any of the electrodes 16 via bus 116, and thus effectively selects the anode and cathode electrodes. In short, buses 118 and 116 generally set the stimulation program the IPG 100 is running. The illustrated stimulation circuitry 105 for producing stimulation pulses and delivering them to the electrodes is merely one example. Other approaches may be found for example in U.S. Pat. Nos. 8,606,362 and 8,620,436.

Notice that the current paths to the electrodes 16 include the DC-blocking capacitors 107 alluded to earlier, which as known provide additional safety by preventing the inadvertent supply of DC current to an electrode and to a patient's tissue. As discussed earlier, capacitances such as these can become charged as stimulation currents are provided, providing the impetus for the use of biphasic pulses.

Any of the electrodes 16 can preferably be used to sense the ECAP described earlier, and thus each electrode is further coupleable to at least one sense amp 110. In the example shown, all of the electrodes share a single sense amp 110, and thus any one sensing electrode can be coupled to the sense amp 110 at a given time per multiplexer 108, as controlled by bus 114. This is however not strictly necessary, and instead each electrode can be coupleable to its own dedicated sense amp 110. The analog waveform comprising the ECAP, described further below, is preferably converted to digital signals by an Analog-to-Digital converter 112, which may also reside within the control circuitry 102.

Notice that connection of the electrodes 16 to the sense amp(s) 110 preferably occurs through the DC-blocking capacitors 107, such that capacitors are between the electrodes and the sense amp(s). This is preferred so as to not undermine the safety provided by the DC-blocking capacitors 107.

Once the digitized ECAP is received at the control circuitry 102, it is processed by the ECAP algorithm 124 to determine one or more ECAP shape parameters. The waveform to the right in FIG. 7 shows the basic shape of an ECAP. Unlike the action potential shown for an individual neuron in FIG. 5, the ECAP measured external to the cell will be inverted, but will otherwise generally resemble the shape of a signal action potential. As it name implies, ECAP comprises a compound (summation) of various action potentials as issued from a plurality of neurons, and it size will thus depend on how many neurons are firing. Generally speaking, an ECAP can vary between 100 microVolts to tens of milliVolts. Note that the DC blocking capacitor 107 through which the ECAPs pass will remove any DC components in the signal, which is thus referenced to 0 Volts. If necessary, the sensed ECAP signal can be level shifted to occur within a range that the electronics in the IPG 100 can handle, such as between 3 Volts and ground.

FIGS. 8A and 8B illustrate a particular stimulation program, the resulting generation of an ECAP, and detection of that ECAP. The stimulation program is defined as before by various stimulation parameters, such as pulses of a particular amplitude, pulse width, and frequency, although these parameters are not labeled in FIG. 8B. In the example stimulation program shown, electrode E4 is selected to operate as an anode (+), and electrode E5 as a cathode (−), as occurred in FIG. 4. It is assumed that this particular stimulation program has been chosen as one that generally provides good therapeutic results for a particular patient, although perhaps with the side effect of paresthesia. This can be said to comprise an "original" stimulation program, may have been determined during ETS testing (FIG. 3) or otherwise.

Once stimulation begins (at time=0), an ECAP will be produced comprising the sum of the action potentials of neurons recruited and hence firing in electric field volume 95. As shown in FIG. 8A, the ECAP will move through the patient's tissue via neural conduction with a speed of about 5 cm/1 ms. In the example shown, the ECAP moves to the right, which is in the direction toward the brain. However, the ECAP will also move in the other direction as well toward the periphery of the patient.

A single sense electrode (S) has been chosen to sense the ECAP as it moves past, which in this example is electrode E9. Selection of an appropriate sense electrode can be determined by the ECAP algorithm 124 operable in the control circuitry 102 based on a number of factors. For example, it is preferable that a sense electrode S be sensibly chosen with respect to the active electrodes, such that the electric field 95 produced around the active electrodes will have ceased by the time the sense electrode is enabled to sense the ECAP. This simplifies ECAP detection at the sense electrode, because voltages present in the electric field 95 will not interfere with and potentially mask the ECAP. In this regard, it is useful for the ECAP algorithm 124 to know the pulse width of the stimulation program, the extent of the size of the electric field 95 (which can be estimated), the speed at which the ECAP is expected to travel, and the distance between electrodes 16 in the electrode array 12, e.g., along a particular straight lead 14 or a paddle lead 15 (FIG. 1A).

In FIG. 8A for example, assume that the pulse width (of both phases of the biphasic pulse) is 0.5 ms as shown, and that electrode E9 is generally 2.5 cm away (d) from the active electrodes (and hence their electric field 95). When the ECAP is formed in the electric field 95 at the outset of stimulation at time=0, it will arrive at electrode E9 after some delay 130 in accordance with the speed at which the ECAP moves (e.g., 5 cm/1 ms). In other words, the ECAP will start to pass sense electrode E9 at 0.5 ms. Because the stimulation pulse and electric field 95 would have ceased at this point, sense electrode E9 should not sense any voltage relating to the electric field, and should only sense the ECAP. Thus, the ECAP algorithm 124 can enable sensing of the ECAP starting at time=0.5 ms after the start of the stimulation pulse. Such enabling can be controlled by controlling multiplexer 108 via bus 114 (FIG. 7) to pass the input from sense electrode E9 to the sense amp 110, the ADC 112, and ultimately the ECAP algorithm 124. Sensing can last for as long as necessary to detect at least some aspects of the shape of the resulting ECAP. For example, sensing can last for a long enough time to allow the polarization and refraction peaks in the ECAP to be detected, which may comprise 3 ms for example.

It should be noted that it is not strictly necessary that sensing occur at an electrode that would not experience interference from the electric field 95, as masking techniques can be used to subtract voltages present in the electric field. Such masking techniques are described for example in M. Hughes, "Fundamentals of Clinical ECAP Measures in Cochlear Implants: Part 1: Use of the ECAP in Speech Processor Programming (2nd Ed.)," Audiology Online (Nov. 8, 2010); and I. Akhoun et al., "Electrically evoked compound action potential artifact rejection by independent component analysis: Technique validation," Hearing Research 302 pp. 60-73 (2013), which are both incorporated herein by reference. Such masking techniques may allow electrodes closer to the active electrodes (e.g., E6) to be chosen as sense electrodes.

Further, the ECAP algorithm 124 could also choose more than one electrode to act as a sense electrode. For example, ECAP algorithm 124 may sense the traveling ECAP at electrodes E6, E7, E8, E9, etc. This would require timing control, because E6 would be sensed before E7, etc., and might further require circuitry changes to accommodate sensing the ECAP at different electrodes at overlapping points in time. For example, each electrode might in this example require its own timing control (mux 108), and its own sense amp 110 and ADC 112, although this isn't illustrated in FIG. 7.

A practical aspect that could affect sensing ECAPs in IPG 100 relates to passive charge recovery. As discussed earlier, the use of biphasic pulses are preferred in an IPG to actively recover charge during the second pulse phase that may have built up across capacitive elements (such as the DC blocking capacitor 107) during the first pulse phase. Because active charge recovery may not be perfect, IPG 100 may additionally include passive charge recovery as implemented by switches 122 shown in FIG. 7. Passive charge recovery switches 122 are controlled by bus 120 issued from the control circuitry 102, and act to connect the inside plate of the DC blocking capacitors 107 to a common potential (Vref). When this occurs, the DC blocking capacitors 107 are connected in parallel between the common potential and the patient's tissue, which helps to equilibrate the charge across the capacitors an hence recover any remaining charge. Passive charge recovery using switches 122 typically occurs after the last phase of each stimulation pulse, as shown by the small, exponentially-decreasing waveform in FIG. 8B. Passive charge recovery might otherwise overlap in time with periods in which ECAP sensing is enabled. This could cause a problem for ECAP sensing, because it would place the common potential on the inputs to the multiplexer that carry the ECAP signals. As a result, control circuitry 102 will preferably not close the passive recovery switch 122 associated with the sense electrode being sensed, although all other switches 122 may be closed. Alternatively, control circuitry may close only the switches coupled to the active electrodes (E4, E5). Once ECAP has been sensed, control circuitry 102 may return to closing the sense electrode's switch 122 if desired.

FIG. 8B illustrates ECAP as sensed assuming two conditions: first, when the recruited neurons within electric field 95 fire in a generally synchronized fashion; and second, when the recruited neurons fire in a generally desynchronized fashion, which as noted before is theorized to be desirable in reducing side effects such as paresthesia. Notice that the shapes of the ECAPs for these two conditions are different. In the synchronized case, the recruited neurons generally fire at the same time, and so their cumulative effect results in a waveform with a higher and sharper peak, that is, in which its height H1 is relatively large, and its full-width half-maximum FWHM1 is relatively small. By contrast, in the desynchronized case, the recruited neurons fire at different times, and so their cumulative effect results in a waveform with a smaller and broader peak in which H2 is relatively small and FWHM2 is relatively large. Other parameters may also be useful in analyzing the ECAP, such as various slopes, the timing of the peaks, etc., but shape parameters H and FWHM are illustrated for simplicity.

Although only one ECAP is shown for each condition shown in FIG. 8B, it should be understood that an ECAP will be produced at the beginning of each stimulation pulse. Thus, the ECAP algorithm 124 may take more than one ECAP measurement—for example, after several consecutive pulses—and average the shape parameters (e.g., H, FWHM) for each. Shape parameters for measured ECAPs taken at different sensing electrodes (e.g., at E6, E7, etc.) can be averaged as well.

Once ECAP has been measured and it shape parameters determined, ECAP algorithm 124 can assess these shape parameters to discern the degree to which stimulation appears to be synchronous or desynchronous, and can automatically adjust the original stimulation program in one or more manners to try and promote desynchronicity. Determining the degree of synchronicity can occur in one simple example by comparing the shape parameters to thresholds, for example, by comparing the height H of the ECAP to a first threshold T1, and/or by comparing the width (e.g., FWHM) of the ECAP to a second threshold T2. Again, other shape parameters can be used, and more than one shape parameter may be considered in determining synchronicity. If it is determined that the ECAP that is too synchronous, for example, if H>T1, and/or if FWHM<T2, then the original stimulation program can be adjusted in one or more manners to try and promote desynchronicity.

Figure 9:
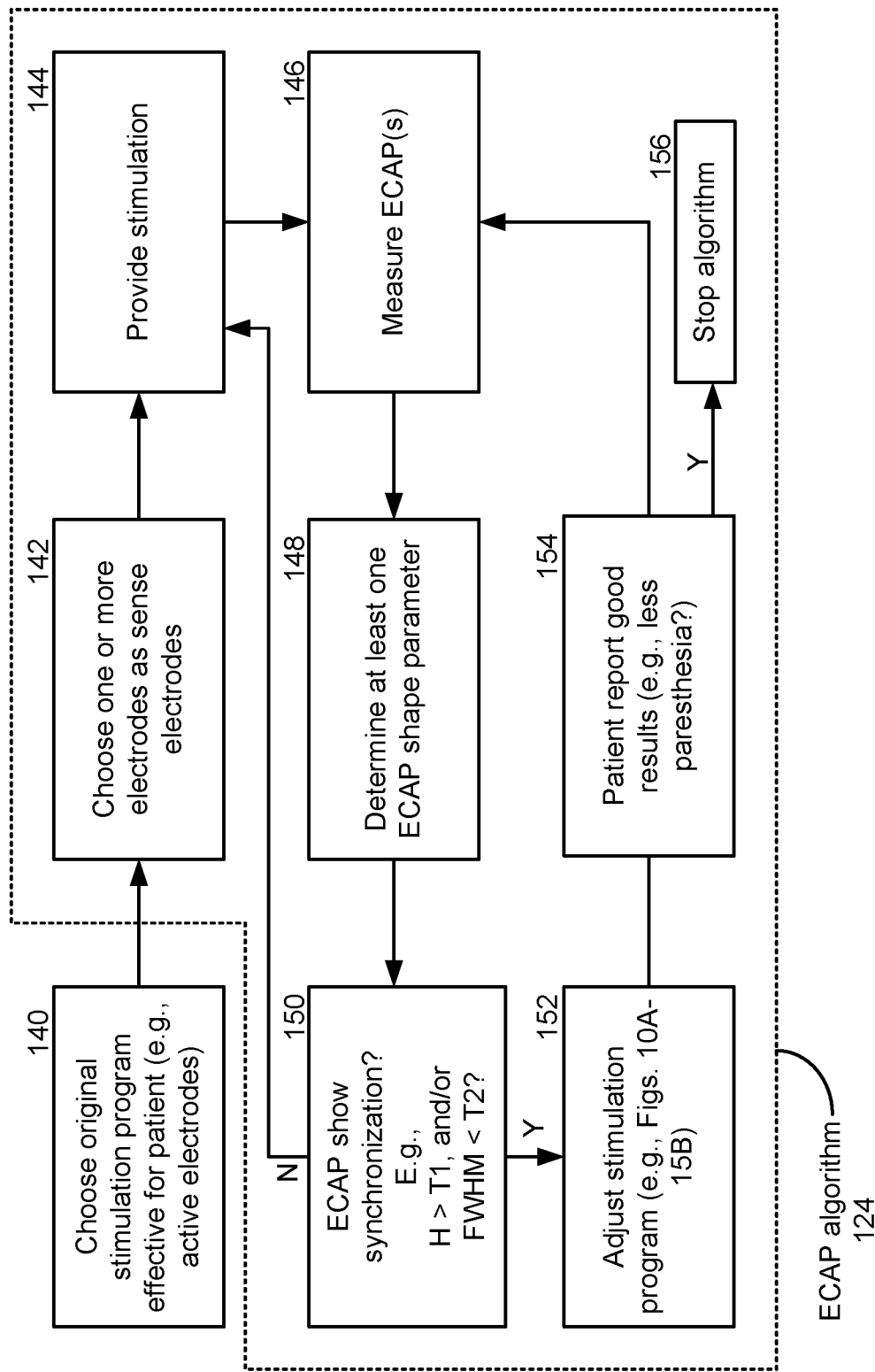
FIG. 9 shows a flow chart of the ECAP algorithm, in accordance with an example of the invention.

FIG. 9 shows an example of the operation of the ECAP algorithm 124, and many of its steps have already been discussed above, but are reviewed here for completeness. Prior to operation of the ECAP algorithm, an original stimulation program has preferably been chosen that is effective for the patient (step 140). This isn't however strictly necessary, and instead the ECAP algorithm 124 may be used in determining an original stimulation program, for example, one that initially seems to provide good desynchronicity during the ETS stage, but which could be modified further later.

Once an original stimulation program is chosen, the ECAP algorithm 124 can choose one or more electrodes to act as a sense electrode (S) (step 142), as described above. Stimulation can then be provided using the original stimulation program (step 144), and one or more ECAP measured (step 146) at the sense electrode(s). As noted above, a plurality of ECAPs can be measured. For the ECAP(s), at least one ECAP shape parameter (e.g., H, FWHM) can be determined (step 148), and if necessary averaged from the plurality of ECAP(s). The ECAP algorithm 124 can then assess the shape parameter(s) to determine a degree of synchronicity of the firing of the recruited neurons (step 150), which may involve comparison of the parameters to one or more thresholds as described earlier.

If the stimulation appears to provide significantly desynchronized firing, the ECAP algorithm 124 can return to step 144 and continue to provide the stimulation program without adjustment, although the process can continue to monitor ECAP and make adjustment in the future if needed. If the stimulation appears to provide significantly synchronized firing, the stimulation program can be adjusted, and manners of doing so are discussed subsequently with respect to FIGS. 10A-15B. Generally speaking, adjustment may involve adjusting any stimulation parameter, including which of the electrodes 16 are to be active; whether those active electrodes are to act as anodes or cathodes; the current or voltage amplitude (A) of the stimulation pulses; the pulse width (PW) of the stimulation pulses; and frequency (f) of the stimulation pulses. After adjustment, ECAP(s) can again be measured (step 146), shape parameter(s) determines (step 148), and assessed (step 150) to see if significant desynchronization has been achieved. If not, the stimulation program can be adjusted again, and the process repeated.

Note that after simulation is adjusted (step 152), an optional step 154 can include inquiring with the patient as to how the adjustment feels, such as whether the adjustment seems to have reduced side effects such as paresthesia. If so, the ECAP algorithm 124 could be stopped at this point (step 156), with the adjustment set as the new stimulation program for the patient. Or, the ECAP algorithm 124 could be allowed to continue to see if even better therapeutic results can be achieved.

While the ECAP algorithm 124 can simply always be operable in the IPG 100 or an ETS, it may be more sensible to enable its use only at various times to improve an original stimulation program otherwise selected for a given patient. Occasional use of the ECAP algorithm 124 can be achieved using any external system that can communicate with the IPG 100 or ETS, such as the clinician programmer system of FIG. 3, or the patient external controller 50 of FIG. 2. Although not shown, such an external system can be programmed with a user interface program executable on an external device configured to communicate with the medical device, which when executed is configured to present an option to allow a user of the external system (e.g., on its screen or display) to command the medical device to implement the ECAP algorithm 124, and perhaps also to disable use of the algorithm.

Further, at least some portions of the ECAP algorithm 124, or all of it, may operate on the external system. For example, the external system's communication circuitry may receive the detected neural response (ECAP); determine the shape parameters and assess them for relative synchronicity; determine how to adjust the original stimulation program to promote desynchronicity; and transmit one or more control instructions to cause the medical device to adjust the stimulation program accordingly. Use of the ECAP algorithm 124 in conjunction with the clinician programming system as the external system can occur during an ETS phase, or even afterwards when an IPG has been fully implanted, such as when a patient meets with a clinician for a check-up.

One skilled in the art will understand that the ECAP algorithm 124 and/or any supporting user interface program will comprise instructions that can be stored on non-transitory machine-readable media, such as magnetic, optical, or solid-state memories. Such memories may be within the IPG or ETS itself (i.e., stored in association with control circuitry 102), within the external system, or readable by the external system (e.g., memory sticks or disks). Such memories may also include those within Internet or other network servers, such as an implantable medical device manufacturer's server or an app store server, which may be downloaded to the external system.

As noted, adjustment of the original stimulation program by the ECAP algorithm 124 to promote desynchronicity (step 152, FIG. 9) can occur in several different manners, some of which are illustrated in FIGS. 10A through 15B. While these manners are described individually for simplicity, it should be noted that any of the manners can be used in combination.

Figure 10A:
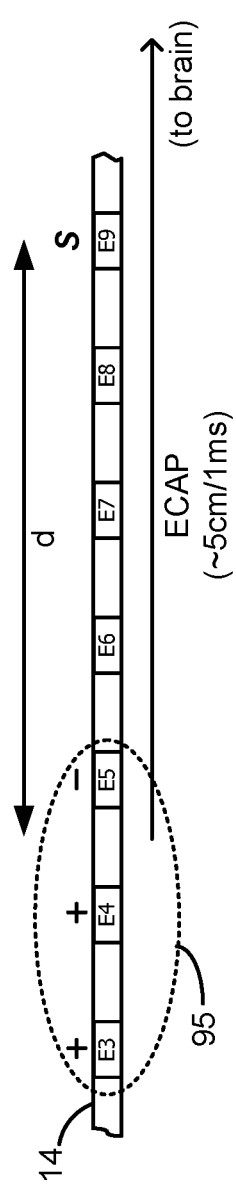
FIGS. 10A and 10B show a first manner in which the ECAP algorithm can adjust the original stimulation program to promote desynchronous firing of recruited neurons through the addition of active electrode, in accordance with an example of the invention.
Figure 10B:
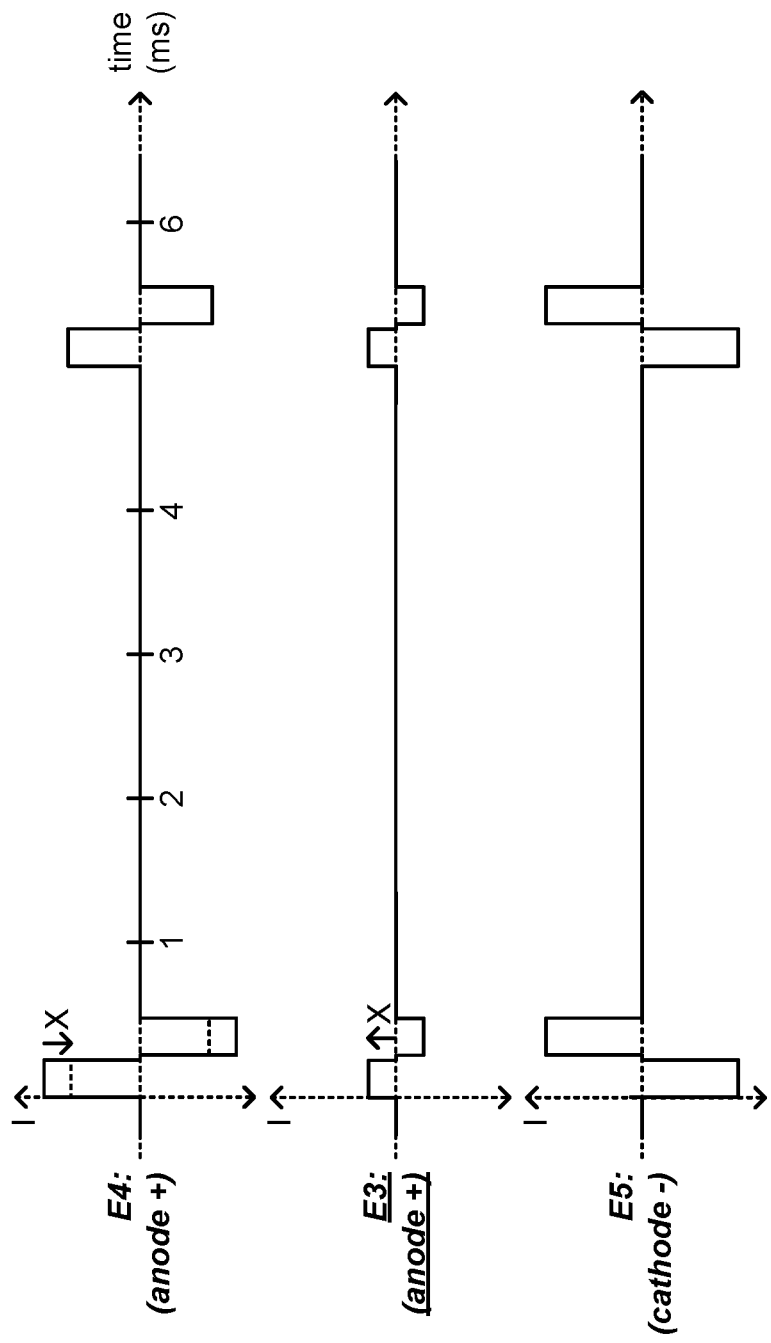

A first manner in which the ECAP algorithm 124 can adjust a patient's original stimulation program to achieve improved desynchronicity is shown in FIGS. 10A and 10B. In this example, the ECAP algorithm 124 has added an additional active electrode to the stimulation program. Specifically, an electrode (E3) has been added to the original stimulation program (which again comprises E4 as an anode and E5 as a cathode in a simple example) as an additional anode. This additional anode (E3) is preferably proximate to the other active electrodes (E4, E5) to be generally consistent with the location of needed therapy, but need not be so. In the example shown, the amplitude of additional anode E3 equals an amount (X) by which the amplitude of anode E4 is decreased. Thus, the ECAP algorithm 124's adjustment to the stimulation program in this example does not vary the energy used to provide stimulation pulses, although this isn't strictly necessary. Anode E4 can retain its original amplitude, with the amplitude of E3 set in other manners. Regardless, note that the cathodic current at cathode electrode E5 may or may not need adjustment to recover the sum of the anodic current at E4 and E3. Notice in this example that additional anode E3 otherwise has the same timing (pulse width, and frequency) as original active electrodes E4 and E5.

As shown in FIG. 10A, and when compared to FIG. 8A, it is seen that adding anode electrode E3 varies the size and shape of the electric field 95 that forms in the patient's tissue. As a result, different neurons will be recruited, and at different lengths along the lead, which should generally increase desynchronicity of the resulting ECAP. Although not shown, whether this adjustment has in fact increased desynchronicity can be verified by the ECAP algorithm 124 by detecting at the designated sense electrode(s) (e.g., E9; FIG. 8B) the shape of the resulting ECAP, as explained earlier. (The resulting ECAP at the sense electrode S is not shown in FIG. 10B for simplicity). If increased desynchronization is sensed, hopefully with the patient reporting good therapeutic results and less paresthesia, the ECAP algorithm 124 can either keep running and making future adjustments as necessary, or the ECAP algorithm 124 may stop running and set the adjustment as the new stimulation program for the patient. If increased desynchronization is not sensed, the ECAP algorithm 124 can continuing running to make other adjustments, such as by picking other additional anodes or cathodes, by varying their amplitudes, or by other means discussed subsequently.

Although not shown in FIGS. 10A and 10B, realize that still another anode could be added by the ECAP algorithm 124 to try and increase desynchronicity, or one or more additional cathodes could be added as well. For example, E3 and/or E6 could be added as an additional cathode.

Figure 11A:
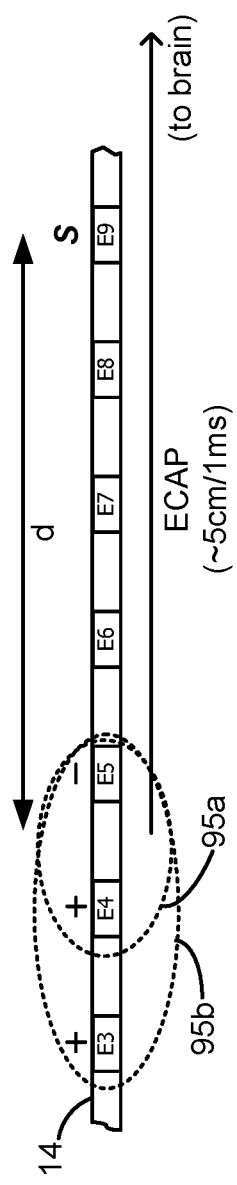
FIGS. 11A and 11B show a second manner in which the additional active electrode produces a pulse that is not overlapping with the pulses in the original stimulation program, in accordance with an example of the invention.
Figure 11B:
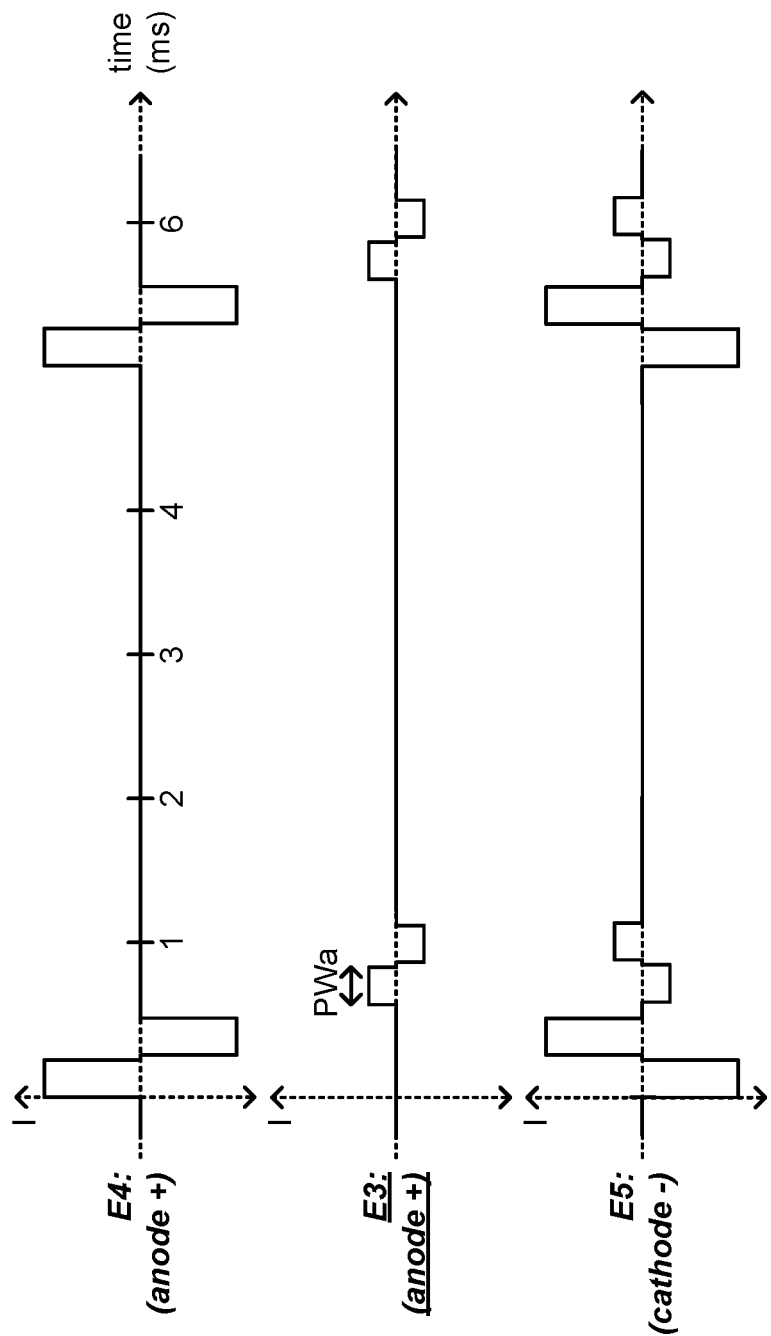

In the example of FIGS. 10A and 10B, additional anode or cathode electrodes issue pulses having the same timing as those specified by the original stimulation program. However, such additional electrodes may also issue with different timings as well, as shown in FIGS. 11A and 11B. In this example, ECAP algorithm 124 has again added an additional anode electrode E3 to try and increase desynchronicity, but the pulse at E3 issues after the pulses otherwise provided by the original stimulation program at electrodes E4 and E5 such that they are non-overlapping. Notice that cathode electrode E5 is concurrently modified by the ECAP algorithm 124 to provide a return path for the added anodic current issued by the additional anode E3. Although not illustrated, a different cathode electrode could be chosen to compliment additional anode electrode E3. In fact, because the additional anode pulse at E3 is non-overlapping, a complementary cathodic pulse could comprise any electrode, including E4, even though E4 otherwise operates as an anode in the original stimulation program. Further, although the additional anode electrode is seen to issue a pulse with a pulse width equal to those used in the original stimulation program, the additional anode pulse width (PWa) could be different.

As shown in FIG. 11A, this example produces two electric fields at two different times: a first field 95a formed during the original pulses (E4 and E5), and a second field 95b formed by the pulses involving the additional anode (E3 and E5). As such, different neurons will be recruited by the different electric fields, and will fire at different points in time. This will increase desynchronicity, as verifiable via the ECAP algorithm 124, hopefully with good therapeutic results and reduced side effects. Again, although not illustrated, one or more additional anodes, or one or more additional cathodes, could be chosen by ECAP algorithm 124 to try and increase desynchronicity. Additional further pulses could also issue that are non-overlapping with the pulses at E3, E4, or E5, although this isn't shown.

Figure 12A:
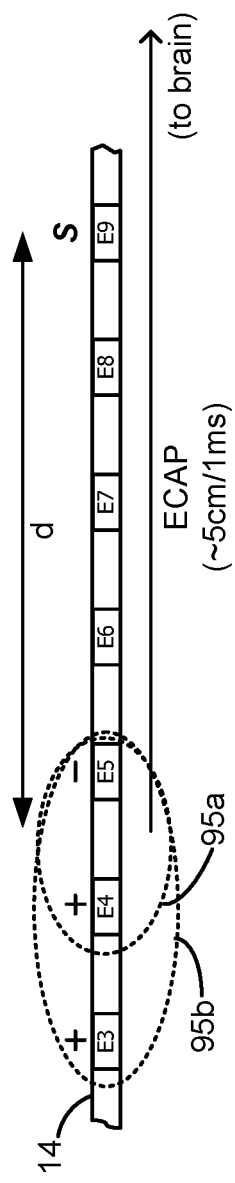
FIGS. 12A and 12B show a third manner in which the additional active electrode produces pulse that are overlapping with the pulses in the original stimulation program, in accordance with an example of the invention.
Figure 12B:
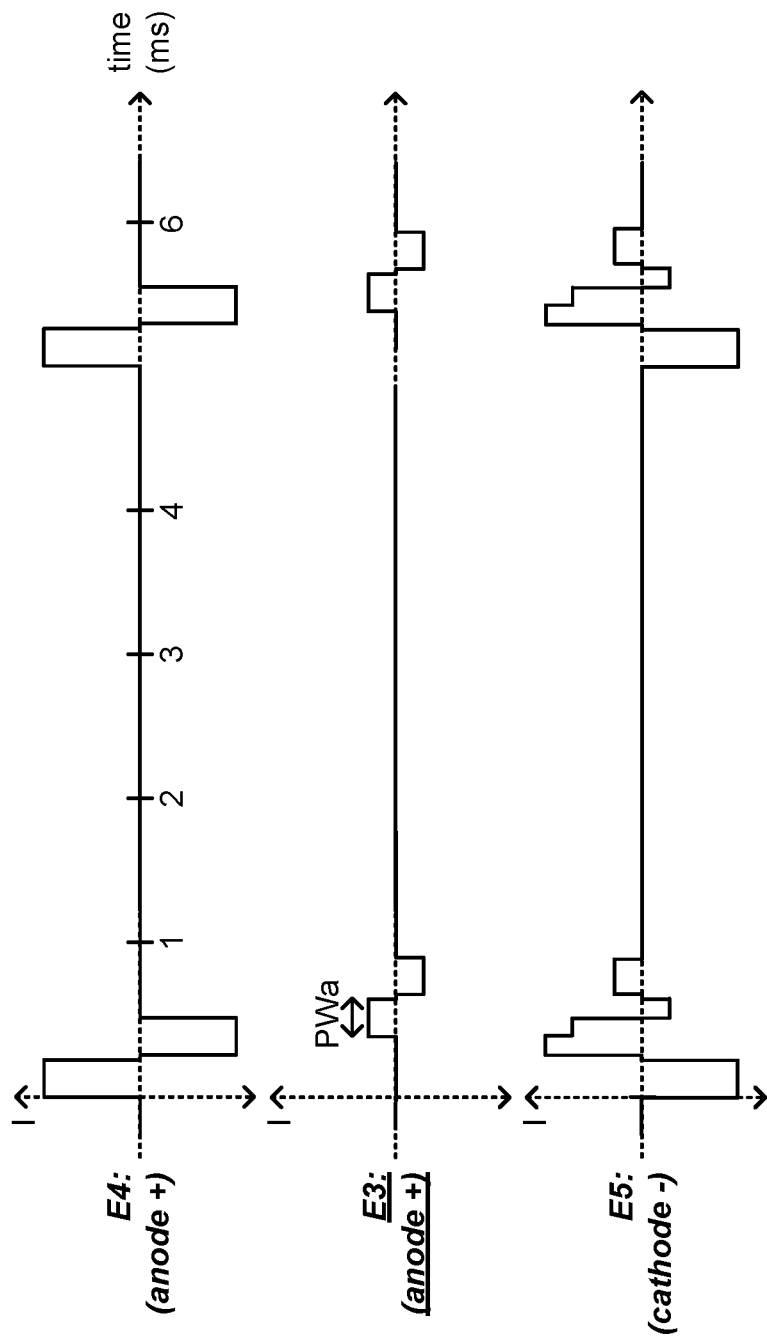

FIGS. 12A and 12B illustrate another manner in which ECAP algorithm 124 can attempt to increase desynchronicity, by choice of an additional anode or cathode electrode that issue a pulse that unlike FIGS. 11A and 11B is at least partially overlapping with the pulses of the original stimulation program. Specifically and as shown, the first phase of the pulse at additional anode E3 overlaps with the second phase of the original stimulation pulses. This is not strictly necessary; the first phase of the additional pulse may overlap with the first phase of the original pulses as well. Further, the pulse width (PWa) of the additional pulse may again be different from the pulse width of the original pulses, as occurred in FIGS. 11A and 11B. Once again, this strategy produces different electric fields between fields 95a and 95b at different points in time, thus recruiting different neurons at different points in time and promoting desynchronicity. Still other overlapping pulses could be added as well.

FIGS. 13A and 13B illustrate an example in which an additional anode issues pulses with a different frequency (f2) than the original stimulation pulses (f1). Again, this will recruit neurons at different times, thus promoting desynchronicity. Again, modifications discussed in conjunction with earlier examples (use of further additional anodes or additional cathode(s), different pulse widths, overlapping or non-overlapping pulses, etc.) could be used here as well.

Promoting desynchronicity via ECAP algorithm 124 may not involve adjustments to an original stimulation program that involve the use of additional anodes or cathodes, as illustrated to this point. Instead, adjustment may involve adjustments using the original active electrodes (e.g., E4 and E5), and a first example is shown in FIGS. 14A and 14B. As shown in FIG. 14B, the ECAP algorithm 124 has adjusted the amplitude (A) of the original pulses to make them different at different points in time. Specifically, the pulses have been adjusted to have a plurality of different amplitudes, and in this example have been split into portions having amplitudes A1 and A2. As shown, A1 and A2 are respectively lower and higher than the original amplitude A by the same amount, and thus require the same energy as the original pulses, but again this is not strictly necessary. The pulse portion of amplitude A1 produces an electric field 95a of a first volume (or strength), while amplitude A2 produces a larger volume (or larger strength) field 95b that would recruit additional neurons, thus promoting desynchronicity in neuronal firing.

In the example of FIGS. 15A and 15B, the adjustment provided by the ECAP algorithm 124 again involves only the original active electrodes E4 and E5, but in which the pulse width of the original stimulation pulses is adjusted from PW to PW1. In this example, the pulse width PW1 is approximately half of the original pulse width PW, and so two biphasic pulses can be formed over the same time duration. This is merely an example though, more than two pulses could be formed, and the pulses formed by adjustment need not occupy the same time duration as the original pulses. Notice in effect that the original pulses in this example have been adjusted into groups (G) of pulses with frequencies (f2) that are higher than the frequency of the original stimulation pulses (f1) in an attempt to increase desynchronicity.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A method for controlling stimulation in a medical device comprising a plurality of electrodes configured to provide stimulation for a patient's tissue, the method comprising:
   (a) issuing stimulation pulses pursuant to a stimulation program at at least two electrodes of the plurality of electrodes, and detecting a first neural response to the stimulation pulses at at least one electrode of the plurality of electrodes different from the at least two electrodes that issue the stimulation pulses;
   (b) determining a shape of the first neural response;
   (c) adjusting the stimulation program to issue adjusted pulses at the at least two electrodes of the plurality of electrodes, and detecting a second neural response to the adjusted pulses at the at least one electrode;
   (d) determining a shape of the second neural response; and
   (e) verifying through a comparison of the first and second shapes that the second neural response is less synchronized than the first neural response.

2. The method of claim 1, further comprising:
   (f) verifying that the adjusted pulses produce less paresthesia in the patient than the stimulation pulses.

3. The method of claim 1, wherein the first and second neural responses comprise Evoked Compound Action Potentials (ECAPs).

4. The method of claim 1, further comprising prior to step (a) selecting the at least one electrode relative to the at least two active electrodes.

5. The method of claim 1, wherein the adjusted pulses have a different amplitude than the stimulation pulses, or wherein the adjusted pulses have a different pulse width than the stimulation pulses, or wherein the adjusted pulses have a different frequency than the stimulation pulses.

6. The method of claim 1, wherein adjusting the stimulation program comprises adding to the at least two active electrodes an additional electrode that issues the adjusted pulses.

7. The method of claim 6, wherein the adjusted pulses at the additional electrode do not overlap with the adjusted pulses at the at least two electrodes.

8. The method of claim 6, wherein the adjusted pulses at the additional electrode overlaps with the adjusted pulses at the at least two electrodes.

9. The method of claim 6, wherein the adjusted pulses at the additional electrode only partially overlap with the adjusted pulses at the at least two electrodes.

10. The method of claim 1, wherein the stimulation pulses have a first frequency, and wherein adjusting the stimulation program comprises issuing the adjusted pulses as groups, wherein each group of the adjusted pulses has a second frequency higher than the first frequency.

11. A system, comprising:
a medical device comprising a plurality of electrodes configured to provide stimulation for a patient's tissue; and
a machine-implementable algorithm, wherein the algorithm when executed is configured to
(a) issue stimulation pulses pursuant to a stimulation program at at least two electrodes of the plurality of electrodes, and detect a first neural response to the stimulation pulses at at least one electrode of the plurality of electrodes different from the at least two electrodes that issue the stimulation pulses;
(b) determine a shape of the first neural response;
(c) adjust the stimulation program to issue adjusted pulses at the at least two electrodes of the plurality of electrodes, and detect a second neural response to the adjusted pulses at the at least one electrode;
(d) determine a shape of the second neural response; and
(e) verify through a comparison of the first and second shapes that the second neural response is less synchronized than the first neural response.

12. The system of claim 11, wherein the algorithm when executed is further configured to
(f) receive an indication that the adjusted pulses produce less paresthesia in the patient than the stimulation pulses.

13. The system of claim 11, wherein the algorithm is stored on a non-transitory machine-readable medium within the medical device, and wherein the algorithm is configured to be executed within the medical device.

14. The system of claim 11, further comprising an external system configured to communicate with the medical device.

15. The system of claim 14, further comprising a user interface program executable on the external system, wherein the user interface program is configured to present an option to allow a user of the external system to command the medical device to implement the algorithm in the medical device.

16. The system of claim 15, wherein the user interface program is further configured to allow the user to disable use of the algorithm in the medical device.

17. The system of claim 14, wherein the algorithm is stored on a non-transitory machine-readable medium within the external system, and wherein the algorithm is configured to be executed within the external system.

18. The system of claim 17, wherein the external system further comprises communication circuitry configured to:
receive the first and second neural responses from the medical device, and
transmit one or more control instructions to control stimulation circuitry in the medical device to issue the adjusted pulses.

19. The system of claim 18, wherein the external system comprises a clinician programmer system or a hand-held external controller for the medical device.

20. The system of claim 11, wherein the medical device comprises an implantable pulse generator or an external stimulator.

* * * * *